United States Patent
Musesti (10) Patent No.: US 9,909,965 B2
(45) Date of Patent: Mar. 6, 2018

(54) PREPARATION DEVICE FOR PREPARING A SAMPLE OF TEXTILE FIBERS, IN PARTICULAR COTTON FIBERS, APPLICABLE TO ANALYSIS AND/OR MEASURING APPARATUSES FOR ANALYZING AND/OR MEASURING CHARACTERISTICS OF THE TEXTILE FIBERS FORMING SAID SAMPLE

(71) Applicant: MESDAN S.p.A., Puegnago del Garda (IT)

(72) Inventor: Fabrizio Musesti, Roe Volciano (IT)

(73) Assignee: MESDAN S.p.A., Puegnago del Garda (IT)

( * ) Notice: Subject to any disclaimer, the term of this patent is extended or adjusted under 35 U.S.C. 154(b) by 0 days.

(21) Appl. No.: 15/334,709

(22) Filed: Oct. 26, 2016

(65) Prior Publication Data

US 2017/0122854 A1  May 4, 2017

(30) Foreign Application Priority Data

Oct. 30, 2015  (IT) .................. 202015000067627

(51) Int. Cl.
*D01G 19/04* (2006.01)
*G01N 3/02* (2006.01)
(Continued)

(52) U.S. Cl.
CPC ............. *G01N 3/02* (2013.01); *G01N 3/08* (2013.01); *G01N 33/365* (2013.01); *D01G 5/00* (2013.01); *D01G 15/24* (2013.01); *D01G 15/46* (2013.01); *D01G 15/80* (2013.01); *D01G 19/00* (2013.01); *D01G 19/06* (2013.01); *D01G 19/10* (2013.01);
(Continued)

(58) Field of Classification Search
CPC ...... D01G 99/005; D01G 15/24; D01G 15/46; D01G 15/80; D01G 5/00; D01G 19/00; D01G 19/06; D01G 19/10; D01G 19/105; D01G 19/12; D01G 21/00; G01N 33/362;
(Continued)

(56) References Cited

U.S. PATENT DOCUMENTS

| | | | | |
|---|---|---|---|---|
| 2,831,216 A | * | 4/1958 | Giovanni Brusorio | D01G 19/16 19/218 |
| 3,718,944 A | * | 3/1973 | Clark | D01G 19/02 19/123 |

(Continued)

*Primary Examiner* — Jonathan Dunlap
(74) *Attorney, Agent, or Firm* — Oblon, McClelland, Maier & Neustadt, L.L.P.

(57) ABSTRACT

A preparation device prepares a sample of textile fibers, in particular cotton fibers, applicable to analysis and/or measuring apparatuses respectively for analyzing and/or measuring characteristics of the textile fibers forming the sample. The preparation device includes a comb body that can be coupled in a sliding manner along a rectilinear guide that faces a perforated plate against which to press a mass of textile fibers forming protuberances projecting from the holes of the perforated plate. The comb body is arranged to grip tufts of textile fibers from such protuberances. The preparation device also includes at least one brush that is mounted in a sliding manner along a rectilinear guide facing the perforated plate and that is arranged to brush the textile fibers forming the protuberances before the comb body grips the tufts.

15 Claims, 6 Drawing Sheets

(51) Int. Cl.
*G01N 33/36* (2006.01)
*G01N 3/08* (2006.01)
*D01G 19/10* (2006.01)
*D01G 19/00* (2006.01)
*G01N 1/28* (2006.01)
*D01G 15/24* (2006.01)
*D01G 5/00* (2006.01)
*D01G 19/06* (2006.01)
*D01G 19/12* (2006.01)
*D01G 21/00* (2006.01)
*D01G 99/00* (2010.01)
*D01G 15/80* (2006.01)
*D01G 15/46* (2006.01)
*G01N 1/04* (2006.01)

(52) U.S. Cl.
CPC ........... *D01G 19/105* (2013.01); *D01G 19/12* (2013.01); *D01G 21/00* (2013.01); *D01G 99/005* (2013.01); *G01N 1/04* (2013.01); *G01N 1/286* (2013.01); *G01N 33/362* (2013.01); *G01N 2203/028* (2013.01); *G01N 2203/0298* (2013.01)

(58) Field of Classification Search
CPC ........ G01N 33/365; G01N 1/04; G01N 1/286; G01N 2203/028
USPC .. 73/160, 159, 864.42, 826, 863.92, 864.41, 73/37.7, 828, 830, 833, 83, 5, 863.91; 19/115 R, 215, 220, 221, 223, 224
See application file for complete search history.

(56) References Cited

U.S. PATENT DOCUMENTS

| | | | | |
|---|---|---|---|---|
| 4,554,709 A * | 11/1985 | Bianchi | ............... | D01H 5/02 19/129 A |
| 4,703,431 A * | 10/1987 | Sako | ............... | D01H 5/42 19/240 |
| 5,178,020 A * | 1/1993 | Elam | ............... | G01N 1/04 73/864.42 |
| 5,333,357 A * | 8/1994 | Duncan | ............... | D01G 15/80 19/107 |
| 5,367,747 A * | 11/1994 | Shofner | ............... | D01G 99/00 19/65 R |
| 5,483,844 A * | 1/1996 | Shofner | ............... | D01G 99/00 73/864.42 |
| 5,491,876 A * | 2/1996 | Shofner | ............... | D01G 99/00 19/129 R |
| 6,085,584 A * | 7/2000 | Ramachandran | ...... | G01N 33/36 73/159 |
| 6,161,441 A * | 12/2000 | Ghorashi | ............... | D01G 99/00 19/19 |
| 6,598,267 B2 * | 7/2003 | Shofner | ............... | D01G 31/006 19/65 R |
| 7,143,642 B1 * | 12/2006 | Baxter | ............... | G01N 33/362 73/159 |
| 7,418,767 B2 * | 9/2008 | Ramachandran | ........ | G01N 3/08 19/215 |
| 2006/0179932 A1 * | 8/2006 | Ramachandran | ........ | G01N 3/08 73/160 |

* cited by examiner

PREPARATION DEVICE FOR PREPARING A SAMPLE OF TEXTILE FIBERS, IN PARTICULAR COTTON FIBERS, APPLICABLE TO ANALYSIS AND/OR MEASURING APPARATUSES FOR ANALYZING AND/OR MEASURING CHARACTERISTICS OF THE TEXTILE FIBERS FORMING SAID SAMPLE

The present invention refers to a preparation device for preparing a sample of textile fibers, in particular cotton fibers, applicable to analysis and/or measuring apparatuses respectively for analyzing and/or measuring characteristics, for example structural, physical or mechanical characteristics, of the textile fibers forming the sample thus prepared.

The present invention also refers to an analysis and/or measuring apparatus respectively for analyzing and/or measuring characteristics, for example structural, physical or mechanical characteristics of textile fibers, in particular cotton fibers, comprising such a preparation device.

The present invention refers, in particular, to a preparation device for preparing a sample of textile fibers, in particular cotton fibers, for preparing a sample of textile fibers in the form of a "beard", i.e. wherein the sampled textile fibers are arranged substantially coplanar to one another to form a line.

The present invention refers, in particular, to a measuring apparatus for measuring the length and/or the dynamometric characteristics of textile fibers, in particular cotton fibers, comprising such a preparation device for preparing a sample of textile fibers in the form of a "beard".

BACKGROUND

Apparatuses for measuring characteristics of cotton fibers are known, which are provided with a preparation device for preparing the sample of fibers to be tested, wherein the sample picked up is in the form of a "beard". In these known apparatuses, the preparation device for preparing the sample comprises a pair of plates that face one another, are parallel and movable relatively to one another; one of these two plates is perforated and arranged at a lower height with respect to the other that, on the other hand, is coupled to actuator means towards and away from the other.

Below the perforated plate a comb is arranged, which is guided in a movable manner in both senses along at least one translation direction.

A mass of cotton fibers is interposed between the two plates and pressed between them so that protuberances of fibers project from the holes of the lower plate. The comb is made to slide below the perforated plate so that its teeth meet the protuberances of fibers projecting therefrom in order to grip tufts of fibers from them. The tufts of fibers gripped by the comb are then carded and brushed, respectively by a card and by a brush, in order to eliminate excess fibers not properly anchored to the teeth of the comb from them and to parallelize the fibers "hooked/fastened" to the teeth of the comb forming a sample of fibers in the form of a "beard", i.e. in which the fibers are substantially coplanar and parallel to one other.

The comb supporting the "beard" of fibers thus sampled introduces the latter into measuring devices for measuring their characteristics like, for example, devices for measuring the length and/or the dynamometric characteristics (i.e. elongation and resistance at break by tension).

BRIEF SUMMARY

The purpose of the present invention is to provide a preparation device for preparing a sample of textile fibers, in particular cotton fibers, applicable to analysis and/or measuring apparatuses respectively for analyzing and/or measuring characteristics of the textile fibers forming the sample thus prepared, which allows improving the quality of the sample picked up, quality on which the measurements carried out on it afterwards depend.

Another purpose of the present invention is to provide a preparation device for preparing a sample of textile fibers, in particular cotton fibers, applicable to analysis and/or measuring apparatuses respectively for analyzing and/or measuring characteristics of the textile fibers forming the sample thus prepared, that is structurally and constructively simple and that can easily be applied in known devices or apparatuses.

These and other purposes according to the present invention are accomplished by making a preparation device for preparing a sample of textile fibers, in particular cotton fibers, applicable to analysis and/or measuring apparatuses respectively for analyzing and/or measuring characteristics of the textile fibers forming the sample thus prepared.

Further characteristics of a preparation device of a sample of textile fibers, in particular cotton fibers, applicable to analysis and/or measuring apparatuses respectively for analyzing and/or measuring characteristics, for example structural, physical or mechanical characteristics, of the textile fibers forming the sample thus prepared, are disclosed herein.

BRIEF DESCRIPTION OF THE DRAWINGS

The characteristics and advantages of a preparation device for preparing a sample of textile fibers, in particular cotton fibers, applicable to analysis and/or measuring apparatuses respectively for analyzing and/or measuring characteristics of the textile fibers forming the sample thus prepared according to the present invention will become clearer from the following description, given as an example and not for limiting purposes, referring to the attached schematic drawings, in which.

DETAILED DESCRIPTION

With reference to the attached figures, a preparation device for preparing a sample of textile fibers, in particular cotton fibers, according to the present invention, has been wholly indicated with 10.

The device 10 comprises a comb body 11 that can be coupled in a sliding manner along a rectilinear guide 12 that faces a perforated plate 13 against which to press a mass M of textile fibers forming protuberances projecting from the holes of the perforated plate 13, the comb body 11 being shaped and arranged to grip tufts of textile fibers from the protuberances that project from the perforated plate 13 at the face thereof facing towards the rectilinear guide 12 (i.e. with reference to the attached figures, the lower face thereof).

According to the present invention, the device 10 comprises at least one brush 14 that is mounted in a sliding manner in both senses along the rectilinear guide 12 and that is configured and arranged so as to brush the fibers forming the protuberances projecting from the perforated plate 13 before the comb body 11 picks up tufts therefrom.

Advantageously, the brush 14 is coupled to the comb body 11 so as to slide together with it along the rectilinear guide 12, the brush 14 being configured and arranged to brush the textile fibers forming the protuberances before the comb body 11 grips tufts thereof.

The brush 14 is coupled to the comb body 11 at the rear or front side thereof, where "rear" and "front" are meant to refer to the sliding sense V of the comb body 11 for picking up tufts of textile fibers from the protuberances projecting from the perforated plate 13, i.e. the sliding sense V of the active stroke of the comb body 11, by "active stroke" meaning the stroke of the comb body 11 during which it picks up tufts of fibers from the protuberances projecting from the lower face of the perforated plate 13.

In greater detail, the device 10 comprises a support structure 15 to which the perforated plate 13 is coupled, the latter being crossed by a plurality of holes or openings that can be of different shapes and sizes. The perforated plate 13 is generally parallel to the ground or in any case to the support plane of the device 10 and, generally, horizontal.

The rectilinear guide 12 is coupled to the support structure 15 and is arranged below the perforated plate 13. The comb body 11 is fixed on a slide 16 that is mounted in a sliding manner on the rectilinear guide 12. The slide 16 can be moved manually or by means of a linear actuator 17 controlled by a processing and control unit that is not shown since it is of the known type.

The perforated plate 13 is coupled to the support structure 15 by means of coupling means configured to allow the height adjustment thereof with respect to the plane containing the rectilinear guide 12 and, in particular, to allow independently adjusting the height of its two end portions or edges at which the "active stroke" of the comb body 11 begins and ends. In particular, this allows arranging the end portion or edge of the perforated plate 13 at which the "active stroke" of the comb body 11 begins at a greater height with respect to that of the end portion or edge of the perforated plate 13 at which the "active stroke" of the comb body 11 ends. This allows progressively reducing the picking up of fibers during the advancement of the comb body 11 along its "active stroke". These coupling means are not described or shown in detail since they can immediately be understood by the person skilled in the art.

The device 10 also comprises a pressure plate 18 that is arranged parallel to the perforated plate 13 and that faces the face of the perforated plate 13 opposite the one facing towards the rectilinear guide 12 (with reference to the attached figures, the pressure plate 18 is arranged above the perforated plate 13). The pressure plate 18 is coupled to the support structure 15 in a movable manner towards and away from the perforated plate 13 in order to press the mass M of textile fibers against it. In particular, the pressure plate 18 is guided and actuated to slide towards and away from the pressure plate 13 by means of a linear actuator that, in the case shown, is of the cylinder and pneumatic piston type with two stems 19 and 20.

The comb body 11 comprises an elongated support 21 shaped, in general, like a plate, a right angled prism or a rectangular parallelepiped arranged so that its height or length extends orthogonally to the sliding direction defined by the rectilinear guide 12 and parallel to the perforated plate 13. A plurality of teeth of needles 22, which are arranged spaced apart in a line, is fixed to the upper edge of the elongated support 21, i.e. to the edge of the elongated support 21 that faces the perforated plate 13. The teeth or needles 22 extend in a direction parallel to the sliding direction defined by the rectilinear guide 12 and are configured and arranged to intersect the protuberances of fibers projecting from the lower face of the perforated plate 13 during the active stroke of the comb body 11.

In a preferred embodiment, a gripper body 23 can be coupled to the comb body 11 so as to slide together with it along the rectilinear guide 12 and in a rotating manner about a respective rotation axis A between a closed position, in which it is clamped against the comb body 11, and an open position, in which it is away from the comb body 11.

In greater detail, the gripper body 23 is arranged at the front side of the comb body 11, i.e. at the side of the comb body 11 from which the teeth or needles 22 project. The gripper body 23 comprises an elongated base from the upper edge of which a plurality of respective teeth 24 project, which are arranged spaced apart and in a line and which, when the gripper body 23 is in its closed position, are interspersed with the teeth or needles 22. The gripper body 23 is articulated to the slide 16 in a rotating manner about the axis A by means of a support bracket 24. The support bracket 24 is hinged about a pin that defines the axis A and has a first end, to which the gripper body 23 is fixed, and a second end, which is opposite the first and which is articulated to the end of a respective linear actuator 25 mounted on the slide 16 itself.

The brush 14 in turn comprises a rib 26 that extends parallel to the length of the comb body 11, i.e. parallel to the elongated support 21, and from which lines of bristles 27, teeth, piles or similar project, which are adapted to brush the textile fibers forming the protuberances projecting from the perforated plate 13.

Figure 1:
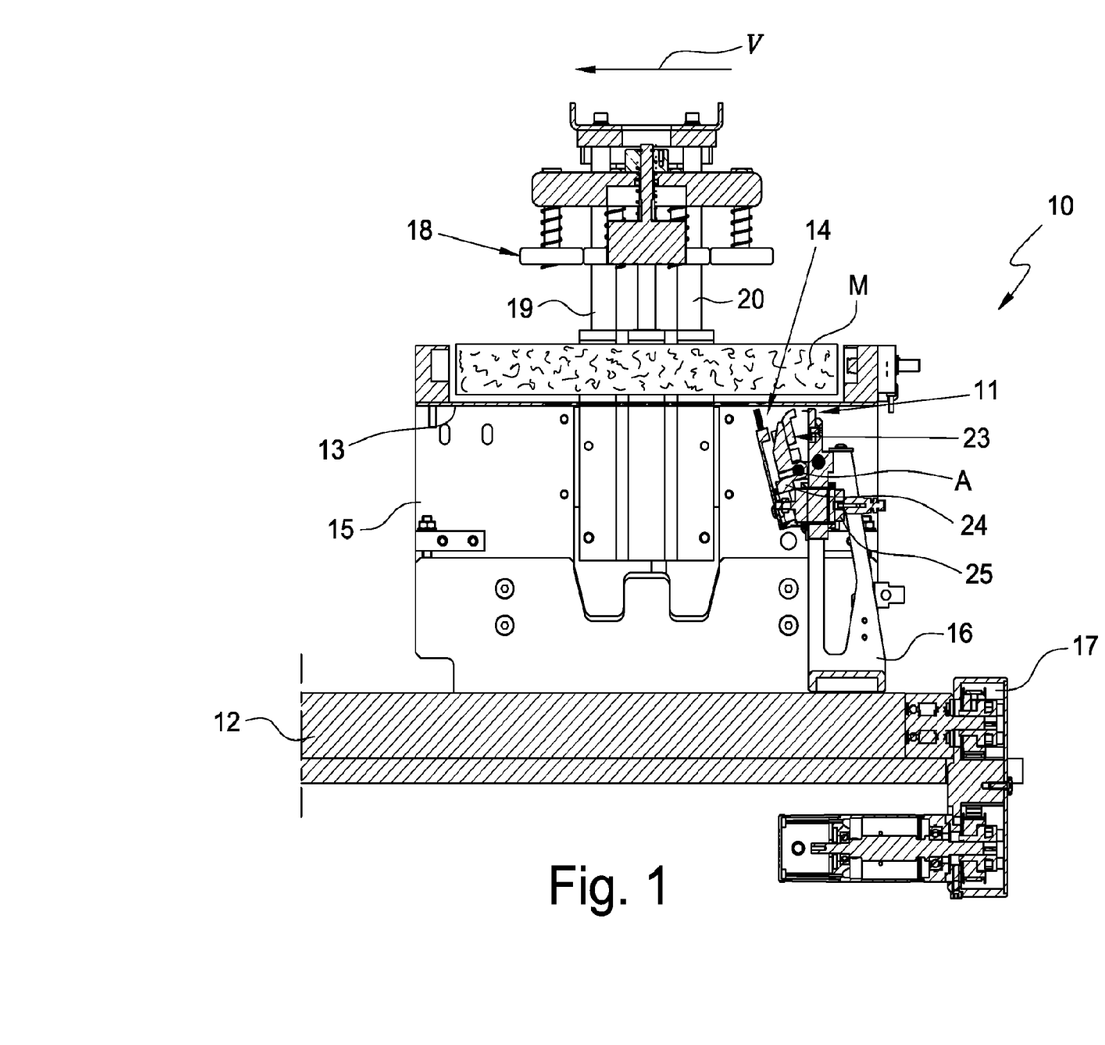
FIG. 1 is a schematic section view of a first embodiment of the preparation device according to the present invention in the starting position for preparing the sample.
Figure 2:
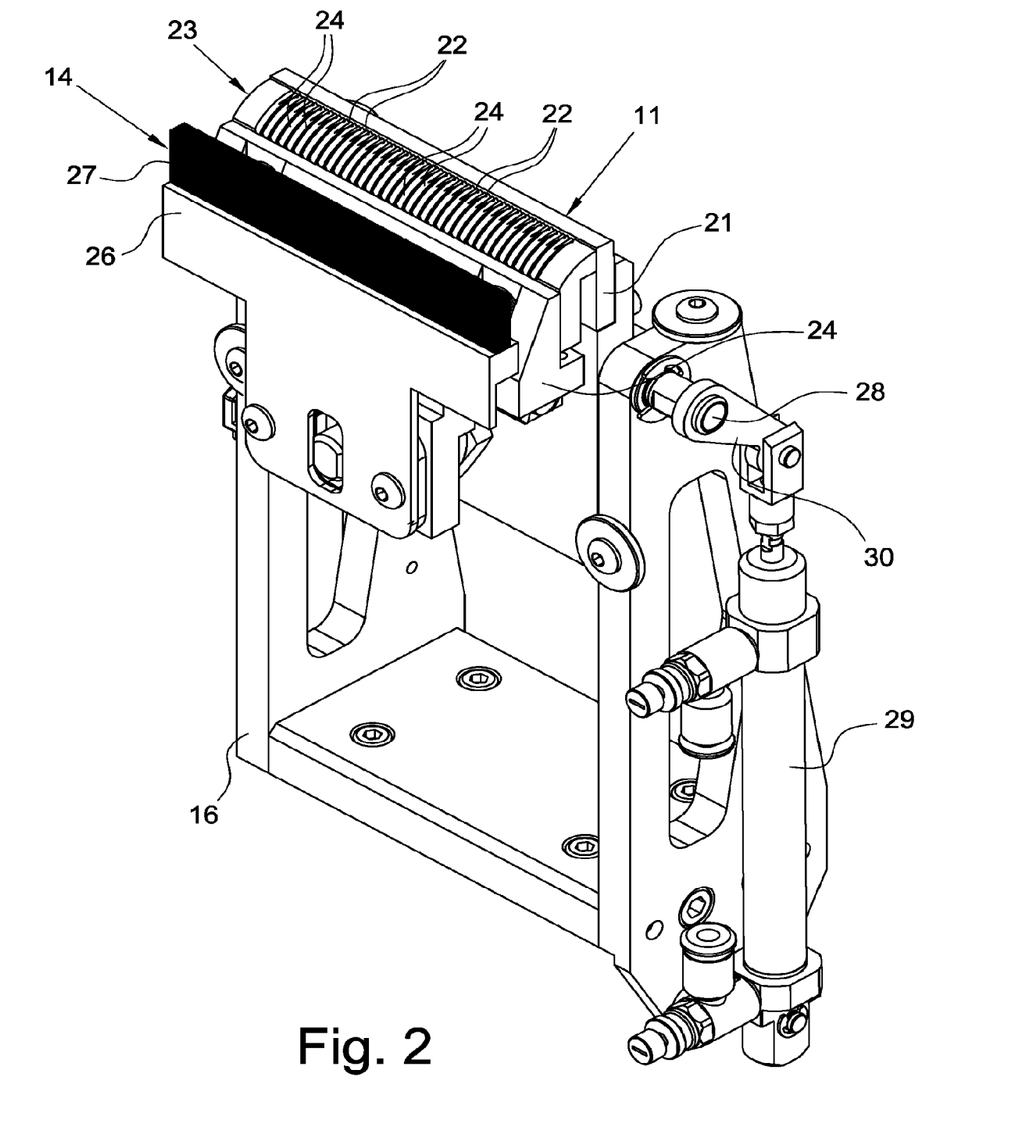
FIGS. 2 and 3 are axonometric views from two opposite sides of a detail of the preparation device of FIG. 1.
Figure 3:
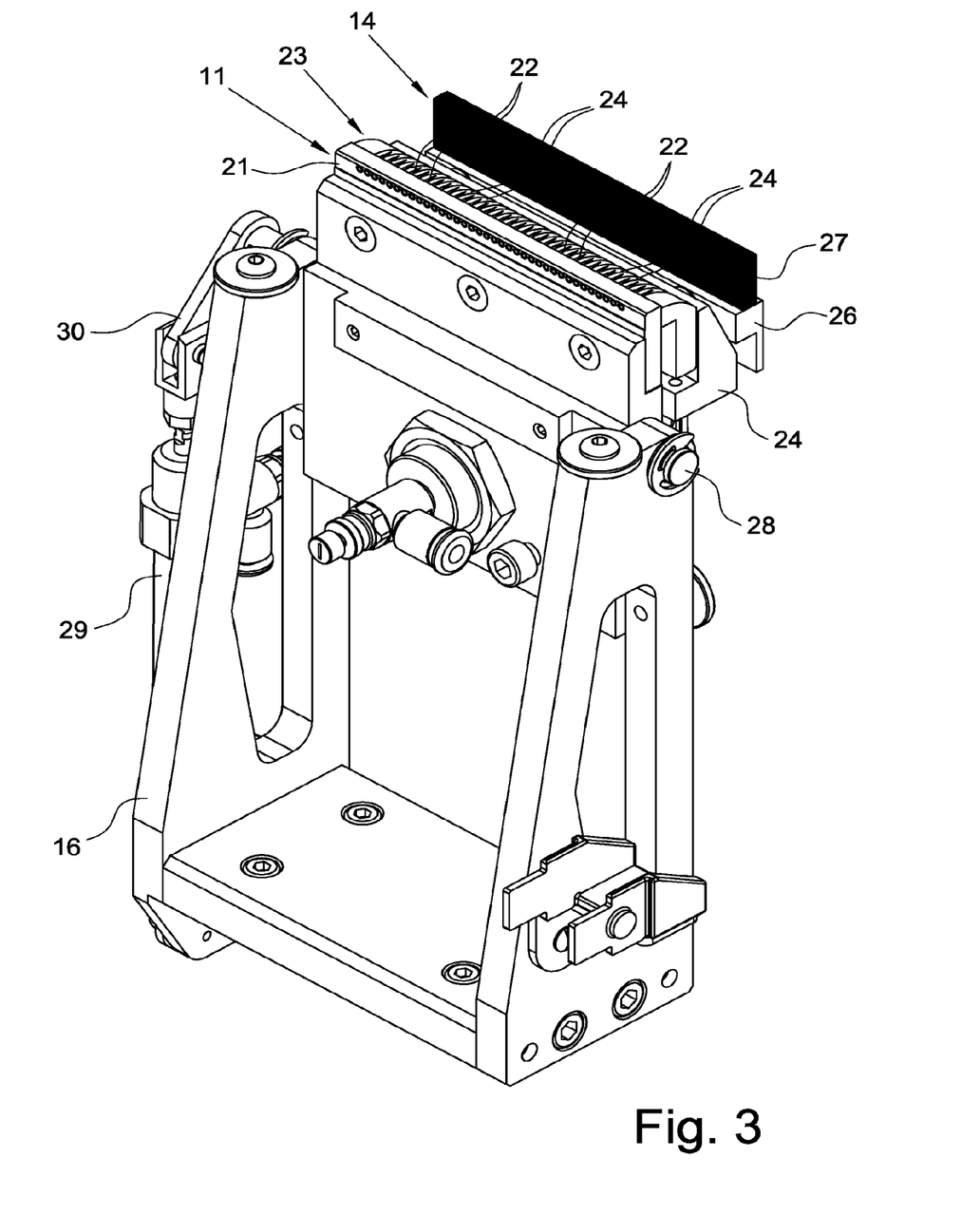

In a possible embodiment, which is represented in FIGS. 1 to 3, the brush 14 is coupled to the comb body 11 at the front side thereof (with respect to the sense V), so that during the same active stroke of the comb body 11, the brush 14, which precedes the comb body 11, brushes the fibers of the protuberances just before the teeth or needles 22 grip tufts thereof.

Advantageously, the brush 14 is fixed to the gripper body 23 and, in particular, it is fixed to the side of the gripper body 23 opposite the one facing the comb body 11. With reference to the embodiment represented in the attached figures, the brush 14 is fixed to the side of the support bracket 24 opposite the one on which the gripper body 23 is fixed.

The brush 14 is thus coupled to the comb body 11 in a movable manner—and, in particular, in a rotating manner about the rotation axis A—between a position close to it (i.e. when the gripper body 23 is in its closed position) and a position away from it (i.e. when the gripper body 23 is in its open position).

In this case, as it can be immediately understood by the person skilled in the art, during the active stroke of the comb body 11, the gripper body 23 is in its open position and the brush 14, preceding the comb body 11, brushes the fibers forming the protuberances projecting from the perforated plate 13 during the active stroke of the comb body 11 just before tufts thereof are gripped or hooked by the teeth or needles of the latter. With reference to the attached FIGS. 1-3, the active stroke of the comb body 11 goes from the right end to the left end, the comb body 11 starting from the right-most position in which it is arranged close to an edge portion of the perforated plate 13, the perforated portion of which extends beyond and in the same sense as the teeth or needles 22.

Figure 4:
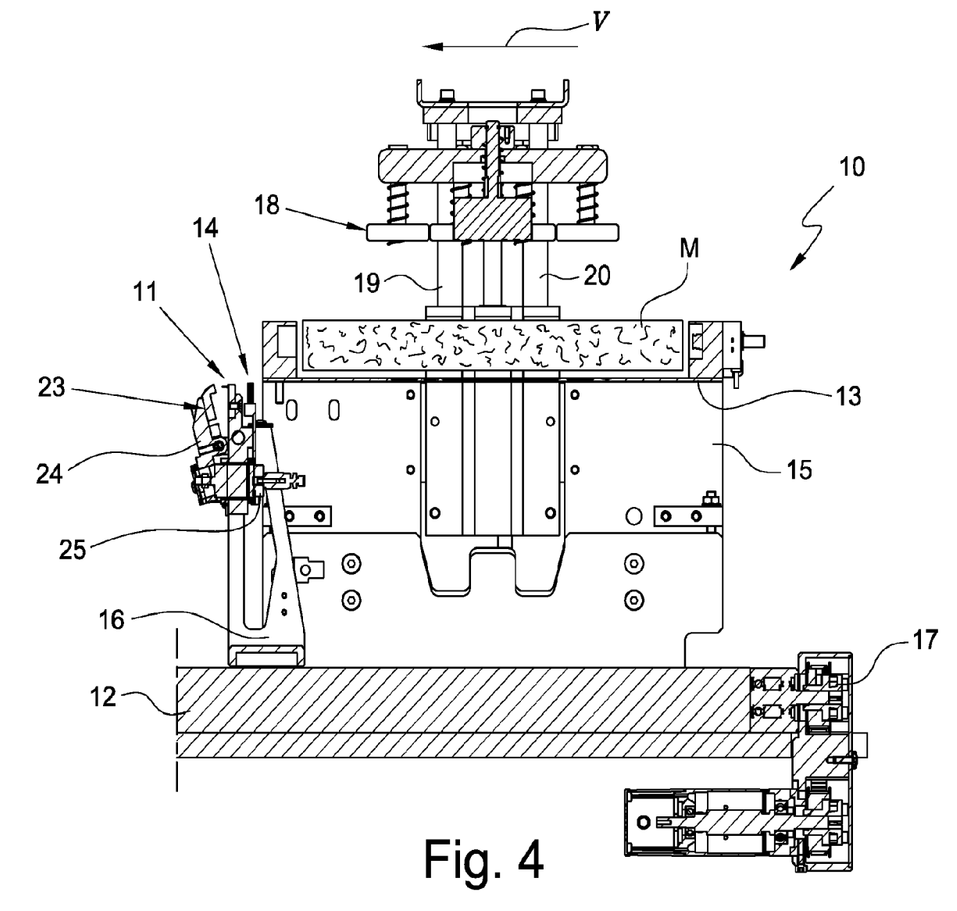
FIGS. 4 and 5 are schematic section views of a second embodiment of the preparation device according to the present invention respectively in the starting position and in a subsequent operative position for preparing the sample.
Figure 5:
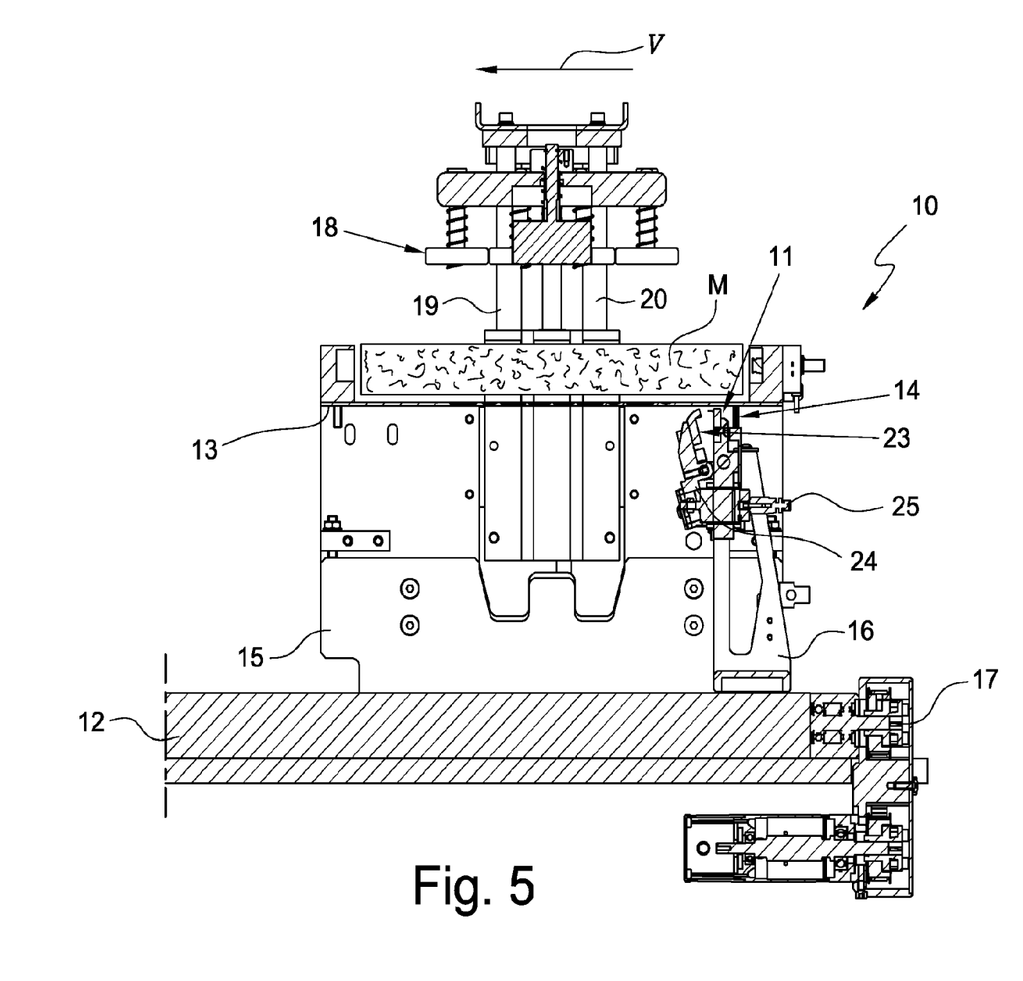

In an alternative embodiment, represented in FIGS. 4 and 5, the brush 14 is coupled to the comb body 11 at the rear side thereof (with respect to the sense V of its active stroke). In this case, the brush 14 can be fixed to the comb body 11 or to the slide 16 that supports it. In this case, moreover, as it will be immediately understood by the person skilled in the art, the comb body 11 carries out two successive strokes from two extreme positions with respect to the perforated plate 13:

a first stroke, in which the comb body 11 starts from a first position, in which it is arranged close to a first edge portion of the perforated plate 13, the perforated portion of which extends beyond and in the sense opposite that of the teeth or needles 22 (in the attached FIGS. 4 and 5, the most left position), and moves towards a second position, in which it is arranged close to a second edge portion of the perforated plate 13, the perforated portion of which extends beyond and in the same sense as that of the teeth or needles 22 (in the attached FIGS. 4 and 5, the most right position), and a second stroke opposite the first, i.e. in which the comb body 11 moves from the second position towards the first (in the attached FIGS. 4 and 5 from right to left).

During the first stroke, the brush 14 brushes the fibers forming the protuberances projecting from the perforated plate 13, the comb body 11 being "inactive", i.e. not gripping any tuft of fibers (the teeth or needles 22 being directed in the sense opposite that of sliding of the comb body 11).

In the second stroke (i.e. the "active stroke"), the comb body 11 grips tufts of fibers from the protuberances projecting from the perforated plate 13.

Also in this case, if the gripper body 23 is present, this is in its open position during the "active stroke" of the comb body 11.

In both the embodiments described above, as soon as the comb body 11 has finished its active stroke picking up tufts of fibers from the protuberances projecting from the perforated plate 13, the gripper body 23 is brought to its closed position in order to clamp the gripped fibers against the comb body 11.

Advantageously, the brush 14 is fixed to the comb body 11, directly or by means of the gripper body 23 or of the support bracket 24 thereof or of the slide 16, in a manner removable and/or adjustable in position.

Finally, in both the embodiments, the comb body 11 —and with it the gripper body 23 and possibly, depending on the case, also the brush 14—is mounted on the bracket 16 in a rotating manner about a pin 28 parallel to the perforated plate 13 and orthogonal to the sliding direction defined by the rectilinear guide 12. A linear actuator 29 mounted on the slide 16, by means of a lever mechanism 30, actuates the rotation of the comb body 11 about the pin 28. In this way, the comb body 11 is rotating between a first position, in which its teeth or needles 22 extend parallel to the perforated plate 13 in order to grip the tufts of fibers from the protuberances projecting therefrom, and a second position (rotated by 90° with respect to the first) in which its teeth or needles 22 extend orthogonally to the perforated plate 13 for example to insert the "beard" sample in a measuring device.

The device 10 is completed by a card 31, arranged to eliminate excess or in any case not properly attached fibers from the tufts hooked by the comb body 11, and by a brush 32 that brushes the tufts of fibers hooked by the comb body 11 by making them substantially coplanar and parallel in order to form a "beard". The card 31 and the brush 32 are arranged in succession along the path of the comb body 11.

Figure 6:
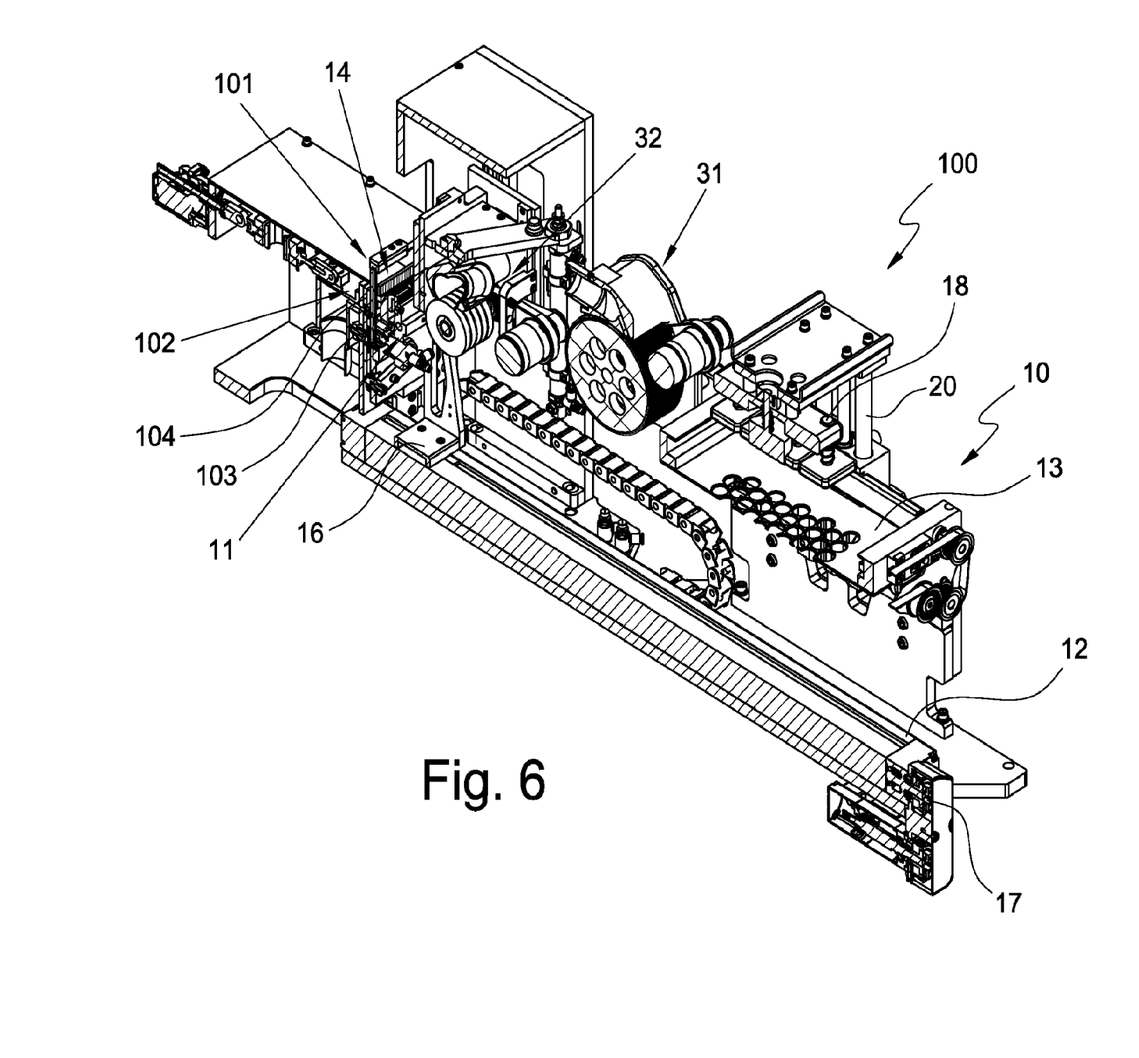
FIG. 6 is a schematic, axonometric and partially sectioned view of a measuring apparatus for measuring characteristics of the textile fibers of a sample provided with a preparation device for preparing the sample according to the present invention.

FIG. 6 shows an analysis and/or measuring apparatus 100 respectively for analyzing and/or measuring characteristics of textile fibers, in particular cotton fibers, comprising a device 10 according to the present invention.

The apparatus 100 is in particular configured for measuring the length and the dynamometric characteristics of the fibers forming the sample picked up by the comb body 11 in the form of a "beard".

The apparatus 100 comprises a first measuring device 101 for measuring the length of the fibers forming the sample picked up by the comb body 11 and a second measuring device 102 for measuring the dynamometric characteristics of the fibers forming the sample picked up by the comb body 11.

The first device 101 and the second device 102 are arranged in succession and downstream of the preparation device 10. The first device 101 can be of the electrical-optical type and is not described here in detail since it is not part of the present invention. The second device 102 is of the dynamometer type and comprises, in totally general terms, a pair of grippers: a fixed gripper 103 and a movable gripper 104 away from and towards the fixed gripper; both the fixed gripper 103 and the movable gripper 104 are arranged to grip respective end portions of the fibers forming the "beard" sample anchored to the comb body 11.

The comb body 11 is relatively movable between the preparation device 10 and an inlet section to the first measuring device 101 and to the second measuring device 102 in order to introduce the "beard" of sampled fibers into them.

The preparation device for preparing a sample of textile fibers, in particular cotton fibers, applicable to analysis and/or measuring apparatuses respectively for analyzing and/or measuring characteristics of the textile fibers forming said sample, object of the present invention has the advantage of preparing the textile fibers forming the protuberances from which the sample is picked up, thus improving the quality thereof and, therefore, the measurements subsequently carried out on it.

Finally, it is clear that the preparation device for preparing a sample of textile fibers, in particular cotton fibers, applicable to analysis and/or measuring apparatuses respectively for analyzing and/or measuring characteristics of the textile fibers forming said sample thus conceived can undergo numerous modifications and variants, all of which are covered by the invention; moreover, all of the details can be replaced by technically equivalent elements. In practice, the materials used, as well as the sizes, can be whatever according to the technical needs.

The invention claimed is:

1. A preparation device for preparing a sample of textile fibers, applicable to analysis and/or measuring apparatuses respectively for analyzing and/or measuring characteristics of the textile fibers forming said sample, wherein the preparation device comprises:

a comb body that can be coupled in a sliding manner along a rectilinear guide that faces a perforated plate against which to press a mass of textile fibers forming protuberances projecting from holes of said perforated plate, wherein said comb body is arranged to grip tufts of textile fibers from said protuberances; and at least one brush that is mounted in a sliding manner along the rectilinear guide facing said perforated plate and that is arranged to brush the textile fibers forming said protuberances before said comb body grips said tufts.

2. The preparation device according to claim 1, wherein said at least one brush is coupled in a sliding manner along said rectilinear guide.

3. The preparation device according to claim 2, wherein said at least one brush is coupled to said comb body so as to slide together with said comb body along said rectilinear guide.

4. The preparation device according to claim 1, wherein said at least one brush is coupled to said comb body at a rear side thereof with respect to a sliding sense of said comb body for picking up said tufts of textile fibers from said protuberances.

5. The preparation device according to claim 1, wherein said at least one brush is coupled to said comb body at a front side thereof with respect to a sliding sense of said comb body for picking up said tufts of textile fibers from said protuberances.

6. The preparation device according to claim 1, wherein said at least one brush is coupled to said comb body in a movable manner between a position close to said comb body and a position away from said comb body.

7. The preparation device according to claim 1, wherein said at least one brush is coupled to said comb body in a rotating manner about a respective axis.

8. The preparation device according to claim 1, further comprising a gripper body that is coupled to said comb body in a rotating manner about a respective rotation axis, wherein said gripper body is movable between a closed position, in which said gripper body is clamped against said comb body, and an open position, in which said gripper body is away from said comb body.

9. The preparation device according to claim 8, wherein said at least one brush is fixed to said gripper body at a side thereof opposite a side facing said comb body.

10. The preparation device according to claim 1, wherein said at least one brush comprises a rib that extends parallel to the length of said comb body and from which lines of bristles, teeth or the like project, which are adapted to brush the textile fibers forming said protuberances.

11. The preparation device according to claim 1, further comprising a support structure to which said perforated plate and said rectilinear guide on which said comb body is guided in a sliding manner are coupled and a pressure plate that faces a face of said perforated plate opposite a face facing towards said rectilinear guide and that is relatively movable towards and away from the perforated plate in order to press said mass of textile fibers against the perforated plate.

12. An analysis and/or measurement apparatus respectively for analyzing and/or measuring characteristics of textile fibers, comprising:
 the preparation device according to claim 1; and
 at least one measuring device for measuring at least one characteristic of the textile fibers forming said sample, wherein said comb body is movable between said preparation device and said at least one measuring device.

13. The apparatus according to claim 12, wherein said at least one measuring device is configured for measuring the length and/or at least one dynamometric characteristic of the textile fibers forming said sample.

14. The apparatus according to claim 12, wherein said textile fibers are cotton fibers.

15. The preparation device according to claim 1, wherein said textile fibers are cotton fibers.

* * * * *